United States Patent
Takahashi et al.

(10) Patent No.: US 8,616,766 B2
(45) Date of Patent: Dec. 31, 2013

(54) CASSETTE FOR RADIOGRAPHIC IMAGING AND CASSETTE LOADING ORIENTATION DETECTION DEVICE

(75) Inventors: Shoji Takahashi, Kanagawa (JP);
Daisuke Utsunomiya, Kanagawa (JP);
Mitsuaki Uchida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 482 days.

(21) Appl. No.: 12/923,507

(22) Filed: Sep. 24, 2010

(65) Prior Publication Data
US 2011/0075817 A1   Mar. 31, 2011

(30) Foreign Application Priority Data

Sep. 25, 2009  (JP) .................................. 2009-220002

(51) Int. Cl.
*H01J 31/49*   (2006.01)
(52) U.S. Cl.
USPC ........................................................ 378/189
(58) Field of Classification Search
USPC ..................... 378/189, 167, 169, 176, 98.8
See application file for complete search history.

(56) References Cited

U.S. PATENT DOCUMENTS

| | | | |
|---|---|---|---|
| 6,282,264 B1 | 8/2001 | Smith et al. | |
| 7,144,157 B2 * | 12/2006 | Dippl et al. | 378/177 |
| 7,507,983 B2 * | 3/2009 | Ishikawa et al. | 250/584 |
| 7,633,077 B2 | 12/2009 | Kito | |
| 7,775,712 B1 * | 8/2010 | Thieman | 378/189 |
| 2004/0169152 A1 * | 9/2004 | Tsutoh et al. | 250/589 |
| 2007/0272873 A1 * | 11/2007 | Jadrich et al. | 250/370.11 |

FOREIGN PATENT DOCUMENTS

| | | |
|---|---|---|
| EP | 0238923 | 3/1987 |
| JP | 10-062877 A | 3/1998 |
| JP | 2002-336225 A | 11/2002 |
| JP | 2005-065992 A | 3/2005 |
| JP | 2005-195653 | 7/2005 |
| JP | 2005-204857 | 8/2005 |
| JP | 2005-261844 | 9/2005 |
| JP | 2005-296091 A | 10/2005 |
| JP | 2008-220481 A | 9/2008 |
| JP | 2008-246102 A | 10/2008 |

OTHER PUBLICATIONS

Decision of Refusal issued by JPO on Oct. 8, 2013, in connection with corresponding Japanese Patent Application No. 2009-220002.

* cited by examiner

*Primary Examiner* — Irakli Kiknadze
(74) *Attorney, Agent, or Firm* — Jean C. Edwards; Edwards Neils PLLC

(57) ABSTRACT

A cassette for X-ray imaging includes a cassette body storing an X-ray detector. Three reflective optical sensors are arranged on an upper end side of a rear surface, which is opposite to a detection surface, of the cassette body. An X-ray detection device for supine-posture imaging has a table. The X-ray detection device includes a tray to which the cassette is loaded. Markers for identifying a loading orientation of the cassette are attached to the tray. The reflective optical sensors read out the markers and detect the loading orientation of the cassette.

13 Claims, 14 Drawing Sheets

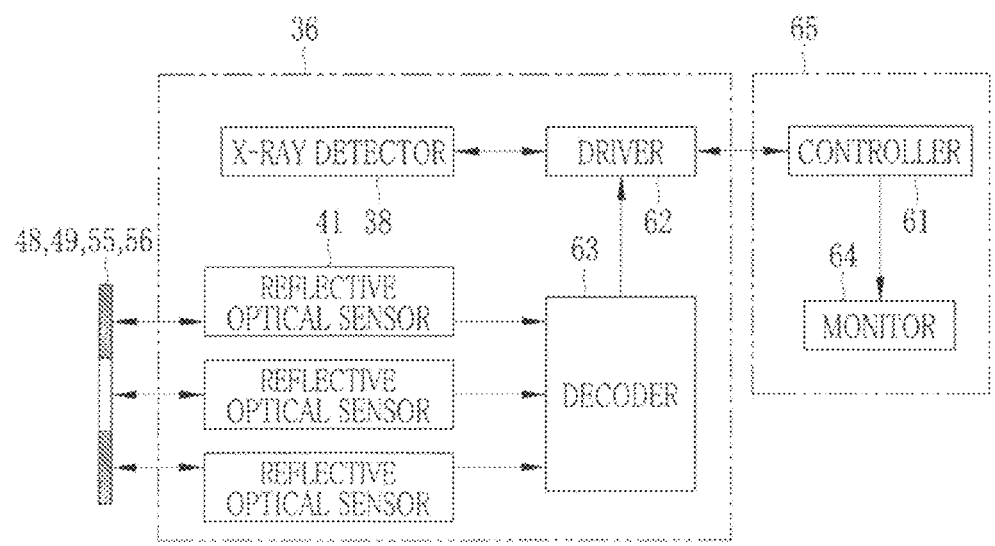

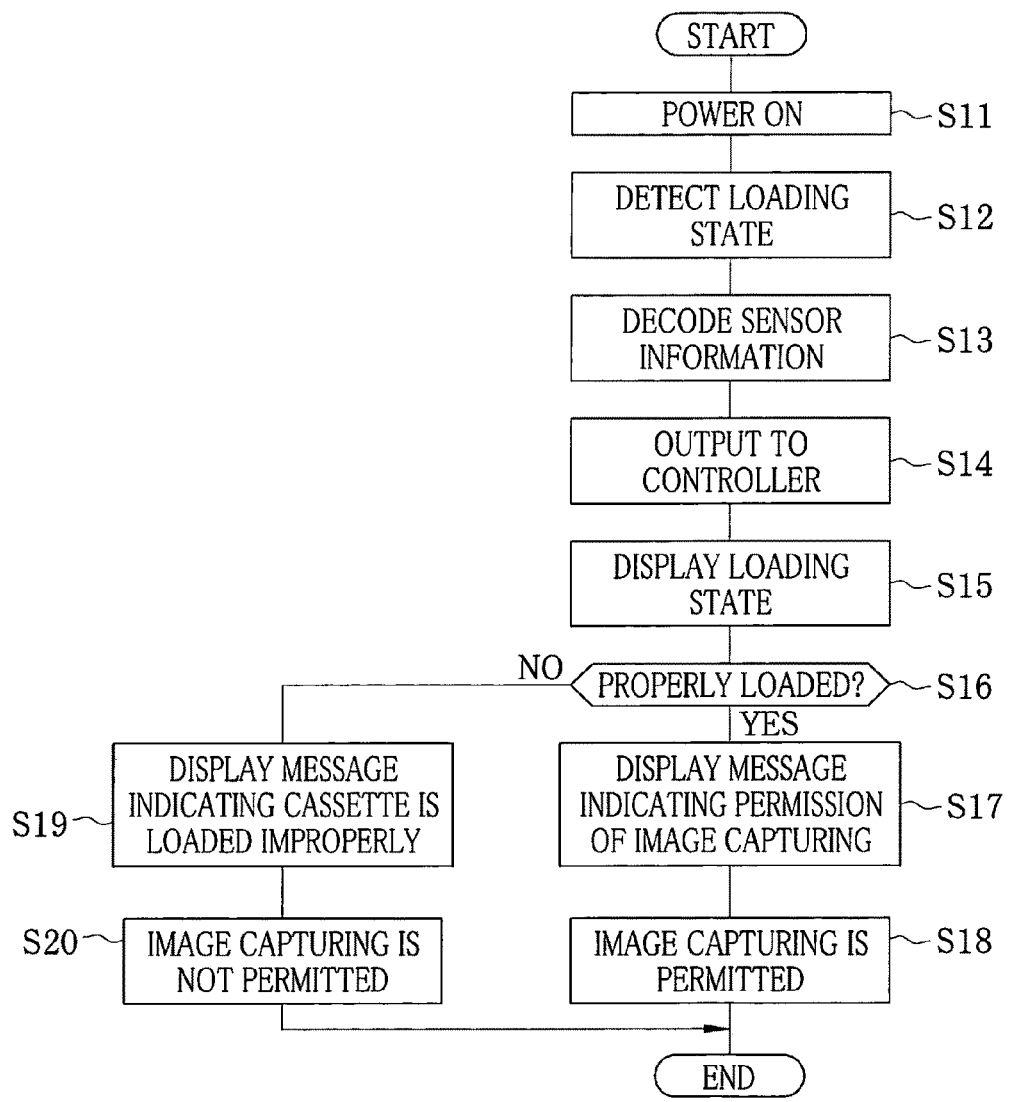

FIG. 8

| MAGNET | NONE | MAGNET |

FIG. 9

| N | S | N |

FIG. 11

| 0 | SUPINE POSTURE, LONGITUDINAL ORIENTATION | |
|---|---|---|
| 1 | SUPINE POSTURE, LATERAL ORIENTATION | |
| 2 | UPRIGHT POSTURE, LONGITUDINAL ORIENTATION | |
| 3 | UPRIGHT POSTURE, LATERAL ORIENTATION | |

FIG. 13

|  | MAGNETIC SENSOR 71 | MAGNETIC SENSOR 72 |
|---|---|---|
| SUPINE POSTURE, LONGITUDINAL ORIENTATION | DETECTED | DETECTED |
| SUPINE POSTURE, LATERAL ORIENTATION | NOT DETECTED | DETECTED |
| UPRIGHT POSTURE, LONGITUDINAL ORIENTATION | NOT DETECTED | NOT DETECTED |
| UPRIGHT POSTURE, LATERAL ORIENTATION | DETECTED | NOT DETECTED |

CASSETTE FOR RADIOGRAPHIC IMAGING AND CASSETTE LOADING ORIENTATION DETECTION DEVICE

CROSS-REFERENCE TO RELATED APPLICATIONS

The present application claims priority from Japanese Patent Application No. 2009-220002, filed Sep. 25, 2009, the contents of which are herein incorporated by reference in their entirety.

BACKGROUND OF THE INVENTION

1. Field of the Invention

The present invention relates to a cassette for radiographic imaging and a cassette loading orientation detection device. The cassette for radiographic imaging stores a radiation detector which detects radiation from a subject.

2. Description of the Related Art

An X-ray imaging system which applies radiation such as X-rays to an examinee as a subject and captures X-ray images is known. The X-ray imaging system has an X-ray detector for detecting X-rays that have passed through the examinee. With use of imaging plate (IP) and flat panel detector (FPD) as the X-ray detector, digital processing of X-ray images have been promoted (see, for example, U.S. Pat. No. 7,633,077 (corresponding to Japanese Patent Laid-Open Publication No. 2008-246102) and Japanese Patent Laid-Open Publication No. 2005-204857.

The IP is stored in a container called cassette, and is taken out from an imaging platform every time an image is captured so as to read out the X-ray image recorded on the IP. The FPD, like the IP, is stored in the cassette. Since the FPD converts the incident X-ray into an electric signal to output, there is no need to take out the FPD every time an image is captured, like the IP. However, since the FPD is very expensive, it is often used in more than one imaging platform (for example, platforms for upright-posture imaging and supine-posture imaging). In this case, the FPD is loaded in the imaging platform before capturing an image.

When the cassette is loaded in wrong orientation, the obtained X-ray image is inverted upside down or rotated vertically or horizontally, and thus the X-ray image cannot be obtained in proper direction. In view of this, a radiation image capturing apparatus of U.S. Pat. No. 7,633,077 judges a loading orientation of a cassette (orientation relative to an imaging platform) according to an orientation of the cassette (absolute orientation) and a posture or attitude of an examinee. Based on the judgment result, an X-ray image in a proper direction can be obtained.

Since the X-ray imaging system is very expensive, the conventional system cannot easily be replaced by the system disclosed in the U.S. Pat. No. 7,633,077. Therefore, it may be considered to apply the invention of the U.S. Pat. No. 7,633,077 to the conventional X-ray imaging system. In this case, however, a sensor for detecting the orientation of the cassette needs to be attached to or incorporated in the cassette, and also the posture of the examinee needs to be input every time an image is captured, which is troublesome. Note that the techniques disclosed in the JP-A 2005-204857 does not aim to detect the orientation of the cassette.

SUMMARY OF THE INVENTION

In view of the foregoing problems, an object of the present invention is to provide a cassette for radiographic imaging and a cassette loading orientation detection device which are applied to the conventional radiographic imaging system with ease and capable of detecting a loading orientation of the cassette.

In order to achieve the above and other objects and advantages of this invention, a cassette for radiographic imaging of the present invention includes a cassette body storing a radiation detector and a sensor or a marker. The cassette body can be loaded in an imaging platform in more than one loading orientation. The sensor detects loading information which includes at least the loading orientation from the marker. When the sensor is provided to the cassette body, the marker is attached to the imaging platform. When the marker is provided to the cassette body, the sensor is attached to the imaging platform.

When the marker is attached to the imaging platform, it is preferable that the marker is located in such a position that the loading information is detected by the sensor of the cassette body loaded in each loading orientation. When the sensor is attached to the imaging platform, it is preferable that the sensor is located in such a position to detect the loading information from the marker of the cassette body loaded in each loading orientation.

It is preferable that the loading information includes information representing whether the imaging platform is an upright-posture imaging platform or a supine-posture imaging platform.

It is preferable that a judgment section is further provided. The judgment section judges a direction of a radiographic image of radiation detected by the radiation detector, based on the loading orientation detected by the sensor.

The sensor or the marker provided to the cassette body is preferably located at an upper end side of the cassette body. The loading information is preferably represented by multiple-bit patterns.

The sensor is preferably one of the following sensors or switch: a reflective optical sensor for judging presence of reflection light, wherein the marker represents 1 bit with black or white; a magnetic sensor for judging presence of magnetism, wherein the marker represents 1 bit with presence of magnet; a magnetic sensor for judging magnetic pole, wherein the marker represents 1 bit with N pole or S pole; and a push button switch for judging presence of pressure, wherein the marker represents 1 bit with presence of a pressing member which presses the sensor.

It is preferable that the marker sends the loading information via radio waves and the sensor receives the radio waves from the marker.

It is preferable that a setup switch is further provided. The setup switch sets either one of an upright-posture imaging platform and a supine-posture imaging platform as the imaging platform.

A cassette loading orientation detection device of the present invention includes a cassette body storing a radiation detector, a marker and a sensor. The cassette body can be loaded in an imaging platform in more than one loading orientation. The marker makes the loading orientation being detected. The sensor detects the loading orientation from the marker. When the sensor is provided to the cassette body, the marker is attached to the imaging platform. When the marker is provided to the cassette body, the sensor is attached to the imaging platform.

It is preferable that a judgment section is further provided to the cassette loading orientation detection device. The judgment section judges a direction of a radiographic image of radiation detected by the radiation detector, based on the loading orientation detected by the sensor.

The present invention enables to detect the orientation of the cassette for radiographic imaging with use of the combination of the sensor and the marker. Therefore, the present invention can be applied to the conventional radiographic imaging system with ease.

BRIEF DESCRIPTION OF THE DRAWINGS

The above objects and advantages of the present invention will become more apparent from the following detailed description when read in connection with the accompanying drawings, in which:

FIG. 5 is a table explaining information represented by markers of 3 bits;

FIG. 6 is a block diagram explaining an electrical configuration of the cassette for X-ray imaging and a console;

FIG. 7 is a flow chart explaining operation process of the X-ray imaging system;

FIG. 8 is an explanatory view of markers of 3 bits, in which 1 bit is represented by a presence of magnet;

FIG. 9 is an explanatory view of markers of 3 bits, in which 1 bit is represented by north pole (N pole) or south pole (S pole);

FIG. 11 is a table explaining information represented by markers of 2 bits;

FIG. 13 is a table explaining relations of the position of the magnetic sensor for detecting magnetism, the position where the cassette for X-ray imaging is loaded, and the loading orientation of the cassette;

DESCRIPTION OF THE PREFERRED EMBODIMENTS

[First Embodiment]

Figure 1:
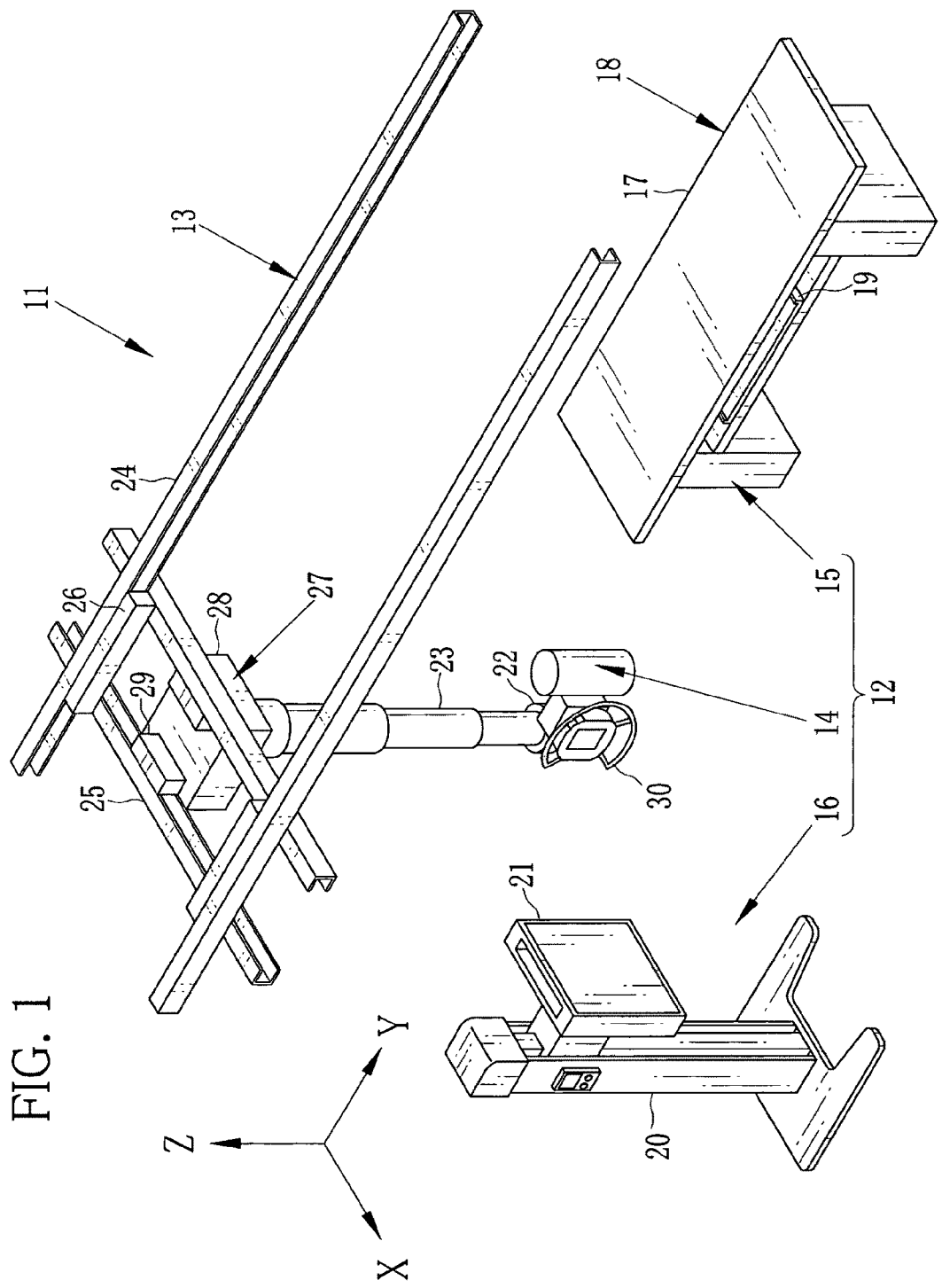
FIG. 1 is a perspective view of an X-ray imaging system.

As shown in FIG. 1, an X-ray imaging system 11 including an imaging apparatus 12 and a moving mechanism 13 is disposed in an X-ray room in a hospital. The X-ray imaging system 11 is capable of capturing images in both upright and supine postures.

The imaging apparatus 12 has an X-ray generator 14 and X-ray detection devices 15, 16. The X-ray generator 14 includes an X-ray tube for emitting an X-ray, a light-emitting part for emitting visible light, and an X-ray movable aperture (collimator) for limiting area being irradiated with the X-ray and the visible light. Before the irradiation of the X-ray, the X-ray generator 14 emits the visible light to the area to be irradiated with the X-ray. Owing to this, the area being irradiated with the X-ray can be confirmed previously.

The X-ray detection device 15 is used for the supine-posture imaging and includes a table 18 having a top plate 17, and a tray 19 to which a cassette for X-ray imaging (hereinafter, referred to as cassette) 36 (see FIG. 2) is loaded. The table 18 works as a supine-posture imaging platform. As an X-ray detector 38 stored in a cassette body 37 (see FIG. 2) of the cassette 36, known imaging plate, flat panel detector, or the like is used.

The X-ray detection device 16 is used for the upright-posture imaging and includes a stand 20 set up on a floor and a holder 21 to which the cassette 36 is loaded. The holder 12 works as an upright-posture imaging platform.

The imaging apparatus 12 captures an X-ray image by detecting an X-ray generated by the X-ray generator 14 with the X-ray detector 38. The captured X-ray image is output to a console 65 (see FIG. 6) and/or a data storage device (not shown).

The X-ray generator 14 is attached to a bottom end of a support post 23 via an arm 22. The support post 23 is extended or contracted in Z-axis (vertical axis) direction. The Arm 22 is rotatable about the Z-axis and a horizontal axis within a predetermined angle range. The X-ray generator 14 moves in the Z-axis direction owing to the extension and contraction of the support post 23. In addition, the X-ray generator 14 changes an irradiation angle owing to the rotation of the arm 22 about each axis.

The moving mechanism 13 moves the X-ray generator 14 between a supine-posture imaging position (see FIG. 1) facing the X-ray detection device 15 for the supine-posture imaging and an upright-posture imaging position (not shown) facing the X-ray detection device 16 for the upright-posture imaging. The moving mechanism 13 includes a pair of fixed rails 24 and a pair of movable rails 25, and a pair of running sections 26 and a carriage 27 which are connected to the rails 24 and 25, and the above-described arm 22 and the support post 23.

The fixed rails 24 are fixed to a ceiling of the X-ray room such that their longitudinal directions extend along a Y-axis direction. The fixed rails 24 have a guide groove and are formed to have a channel-form cross section. Each of the fixed rails 24 is disposed such that its guide groove faces to each other.

The movable rails 25 are attached to the fixed rails 24 via the running sections 26 such that their longitudinal directions extend along the X-axis direction. Like the fixed rails 24, the movable rails 25 have a guide groove. Each of the movable rails 25 is disposed such that its guide groove faces to each other.

Each of the running sections 26 has a rotatable roller (not shown). Owing to the rotation of the rollers in the guide grooves of the fixed rails 24, the running sections 26 move along the fixed rails 24, and this moves the movable rails 25 in the Y-axis direction.

The carriage 27 includes a carriage body 28 and a pair of running sections 29. The carriage body 28 is movably attached to the movable rails 25 via the running sections 29. Each of the running sections 29 has a rotatable roller (not shown). Owing to the rotation of the rollers in the guide grooves of the movable rails 25, the running sections 29 move along the movable rails 25, and this moves the carriage body 28 in the X-axis direction. The support post 23 is fixed to the carriage body 28, and thereby the X-ray generator 14 is suspended from the carriage 27.

The X-ray generator 14 is movably held by the movable rail 25 via the carriage 27. Owing to the movement of the carriage 27, the X-ray generator 14 moves in the X-axis direction. In addition, the X-ray generator 14 moves in the Y-axis direction owing to the movement of the movable rails 25.

The X-ray generator 14 is formed with a control section 30. The control section 30 has a handle for changing posture and position of the X-ray generator 14, and a control panel on which are formed various operation buttons. The rotation and movement of the X-ray generator 14 are manually operated using the handle.

The operation panel has operation buttons such as a break release button. The break stops the X-ray generator 14 at any angle and limits the movement of the X-ray generator 14 by the moving mechanism 13. The break is released while the break release button is pressed. When the break is released, the rotation and movement of the X-ray generator 14 are allowed.

In a control room next to the X-ray room, the console 65 (see FIG. 6) for operating the imaging apparatus 12 is located. The X-ray room and the control room are partitioned with a lead-containing glass. An operator operates the console 65 while looking inside of the X-ray room through the window.

Figure 2:
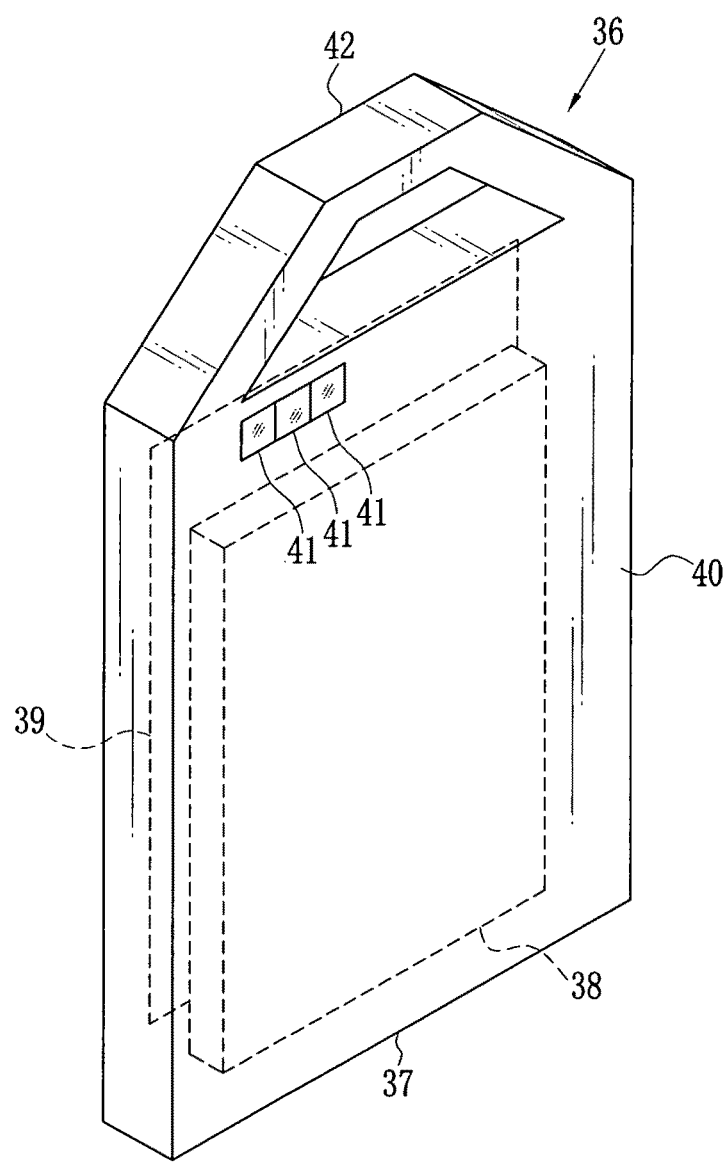
FIG. 2 is a perspective view of a cassette for X-ray imaging.

As shown in FIG. 2, the cassette 36 includes the cassette body 37 which stores the X-ray detector 38. The cassette body 37 has a length of 460 mm and a width of 383 mm and is the same size of the conventional half size IP cassette. The cassette body 37 has a rectangular detection surface 39 which makes the X-ray detector 38 detect the X-ray. The size of the detection surface 39 is slightly smaller than, the cassette body 37, such a size to cover a chest of the examinee.

At an upper end side of a rear surface 40 of the cassette body 37, which is opposite to the detection surface 39, three reflective optical sensors 41 are arranged. The reflective optical sensors 41 detect the position where the cassette 36 is loaded and its loading orientation by detecting markers 48, 49, 55, 56 (see FIGS. 3 and 4) attached to the X-ray detection device 15, 16. The reflective optical sensors 41, as is known, have light-projecting elements and light-receiving elements (both not shown). Light projected from the light-projecting elements is reflected on the markers 48, 49, 55, 56, and the reflected light is received with the light-receiving elements, thereby the position where the cassette 36 is loaded and its loading orientation are detected. The detection by the reflective optical sensors 41 is performed right before an image is capturing as well as at regular time intervals.

Here, the side where the reflective optical sensors 41 are formed is defined as the upper end side of the cassette 36. Since the projected X-ray is read out from the upper end side of the cassette 36 with the X-ray detector 38, the upper end side of the cassette 36 corresponds to an upper end side of the captured X-ray image.

A top of the cassette body 37 is provided with a holding portion 42 which is used for getting the cassette body 37 in and out of the X-ray detection device 15, 16 and for carrying the cassette 36 around.

Figure 3:
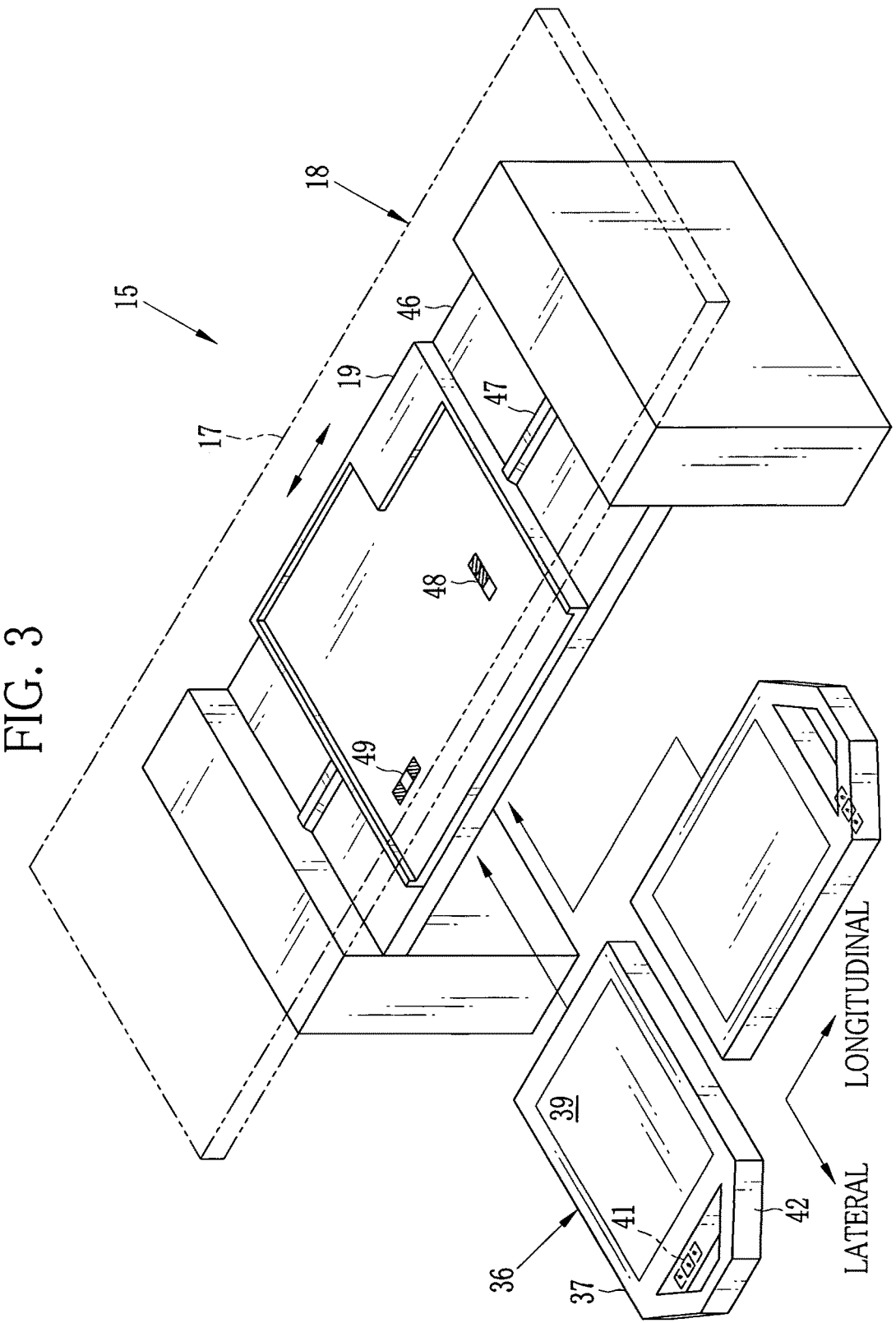
FIG. 3 is an explanatory view of an X-ray detection device for supine-posture imaging.

As shown in FIG. 3, the table 18 has a shelf 46 on which the tray 19 is placed to be parallel with the top plate 17. A rail 47 is laid on the shelf 46 along a longitudinal direction (Y-axis direction shown in FIG. 1) of the table 18. The tray 19 moves on the shelf 46 along the rail 47. Owing to this, the cassette 36 loaded in the tray 19 is moved to a desired imaging position.

The cassette 36 in an orientation along a longitudinal direction of the table 18 (longitudinal orientation) is loaded in the tray 19 from a bottom end side of the cassette 36 where the reflective optical sensors 41 are not arranged. Alternatively, the cassette 36 in an orientation along a widthwise direction of the table 18 (lateral orientation) is loaded in the tray 19 from a lateral side of the cassette 36 where the reflective optical sensors 41 are not arranged.

On the near side of the tray 19 (near an opening through which the cassette 36 is loaded), the markers 48, 49 are attached in such positions to face the reflective optical sensors 41 of the cassette 36 loaded in the longitudinal or lateral orientation. The markers 48, 49 are in a form of adhesive tape, and are attached to the conventional X-ray imaging system. Information on the markers 48, 49 is read out by the reflective optical sensors 41.

Figure 4:
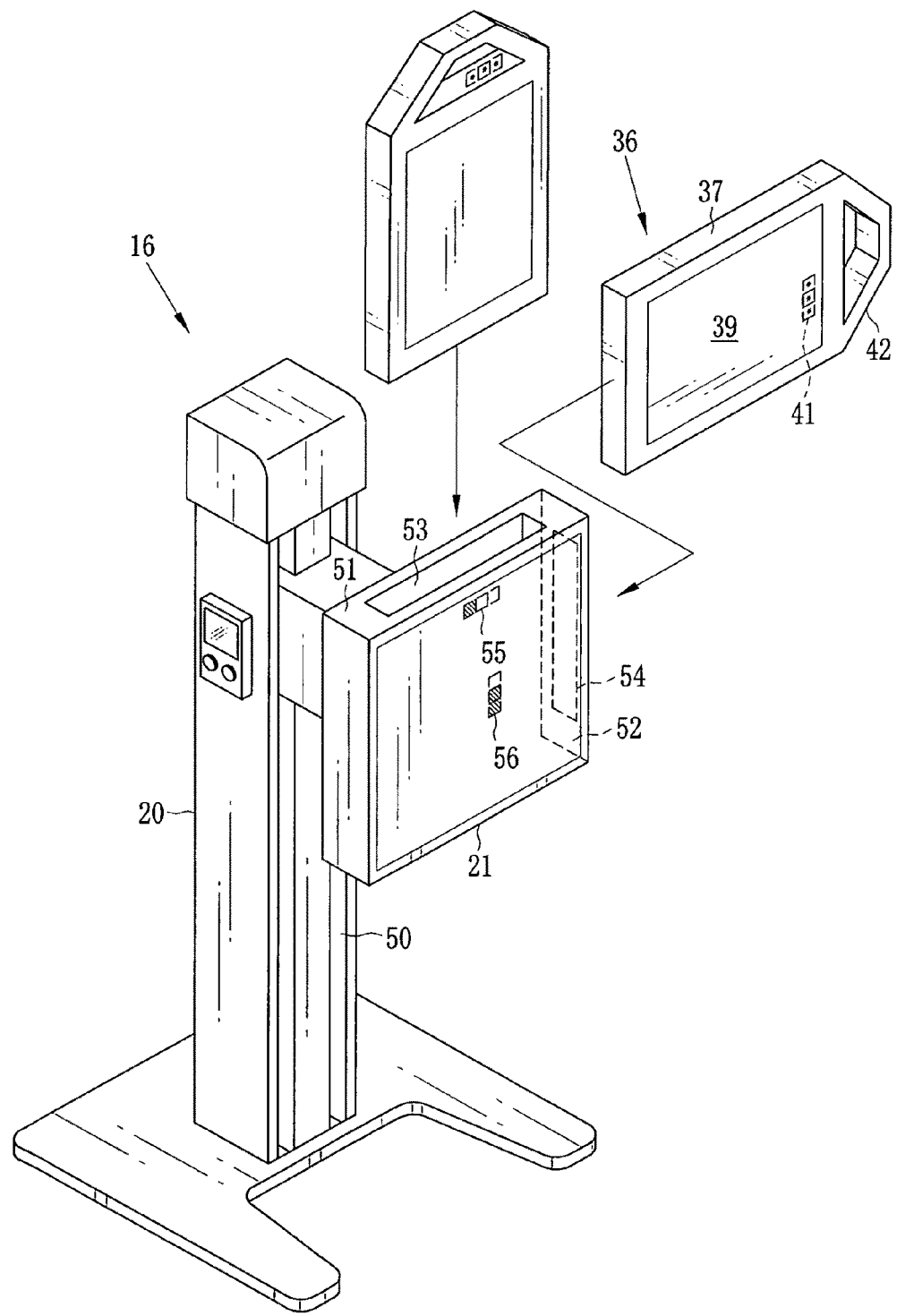
FIG. 4 is an explanatory view of an X-ray detection device for upright-posture imaging.

As shown in FIG. 4, a rail 50 is formed along the vertical direction on the stand 20. The holder 21 is attached so as to be lifted up and down along the rail 50. The holder 21 has a slot 53 on a top surface 51 thereof and a slot 54 on a right side surface 52 thereof. The cassette 36 in the longitudinal orientation is loaded from a bottom end side thereof, where the reflective optical sensors 41 are not arranged, through the slot 53 on the top surface 51. The cassette 36 in the lateral orientation is loaded from the bottom end side thereof, where the reflective optical sensors 41 are not arranged, through the slot 54 on the right side surface 52. The cassette 36 loaded in the holder 21 is moved at a desired height by lifting the holder 21 up and down.

On the near side of the slots 53, 54 of the holder 21, the markers 55, 56 are attached in such positions to face the reflective optical sensors 41 of the cassette 36 loaded in the longitudinal or lateral orientation. The markers 55, 56 have the same configurations as the markers 48, 49, and information on the markers 55, 56 is read out by the reflective optical sensors 41.

Each marker carries information of 3 bits, in which 1 bit is represented by black or white. The marker can represent 8 (=$2^3$) patterns or states. As shown in FIG. 5, the marker 48 represents the state that the cassette 36 is loaded in the table 18, which is for the supine-posture imaging, in the longitudinal orientation with 3 bits of black, black, and white in this arrangement. The marker 49 represents the state that the cassette 36 is loaded in the table 18, which is for the supine-posture imaging, in the lateral orientation with 3 bits of black, white, and black in this arrangement. The marker 55 represents the state that the cassette 36 is loaded in the holder 21, which is for the upright-posture imaging, in the longitudinal orientation with 3 bits of black, white, and white in this arrangement. The marker 56 represents the state that the cassette 36 is loaded in the holder 21, which is for the upright-posture imaging, in the lateral orientation with 3 bits of white, black, and black in this arrangement. The markers 48, 49, 55, 56 make use of difference in contrasting density, however, the markers may use difference in color. For example, the markers may represent information using green and red.

When all of the bits are the same, like the arrangements of black, black, and black or white, white, and white, the marker represents the state that the cassette 36 is not loaded in the table 18 or the holder 21. The marker with the arrangement of white, black, and white, or the arrangement of white, white, and black may be used as spare.

As shown in FIG. 6, the cassette 36 includes a driver 62 and a decoder 63 in addition to the X-ray detector 38 and the reflective optical sensors 41. The driver 62 outputs an image capture signal from the X-ray detector 38 to a controller 61 of the console 65. The decoder 63 decodes the information of the marker detected by the reflective optical sensors 41 into a detection signal.

The decoder 63 decodes the information of 3 bits input from the reflective optical sensors 41. For example, the information on the marker 49 is decoded into a detection signal which represents the state that the cassette 36 is loaded in the lateral orientation in the table 18 for the supine-posture imaging, as shown in FIG. 5. In addition to the image capture signal from the X-ray detector 38, the driver 62 outputs the detection signal decoded by the decoder 63 to the controller 61 of the console 65.

Based on the input detection signal, the console 65 displays information of the cassette 36 on a monitor 64. The information displayed on the monitor 64 includes information on whether the cassette 36 is loaded or not, on which platform the cassette 36 is loaded between the table 18 or the holder 21, on whether the loading orientation of the cassette 36 is one of the predetermined or expected orientations, and the like. If the cassette 36 is loaded in one of the predetermined orientations, the controller 61 allows the image capturing. Once the image is captured, the controller 61 performs various image processing such as tone correction and gamma correction over the image capture signal, and thereby creating an X-ray image. The X-ray image created by the controller 61 is displayed on the monitor 64.

An operation process of the X-ray imaging system 11 is explained with reference to the flowchart of FIG. 7. Upon turning on the X-ray imaging system 11 (step (hereinafter, abbreviated to S) 11), the reflective optical sensors 41 detect the position where the cassette 36 is loaded and its loading orientation, or whether the cassette 36 is loaded or not, according to the information of 3 bits from the marker at regular time intervals (S12).

The information detected by the reflective optical sensors 41 is decoded by the decoder 63 (S13), and then output to the controller 61 of the console 65 via the driver 62 (S14). The information of the cassette 36 output to the controller 61 is displayed on the monitor 64 (S15). If the cassette 36 is loaded in a proper orientation (YES at S16), a message of permission for the image capturing is also displayed on the monitor 64 (S17). Then, the image capturing using the imaging apparatus 12 is allowed (S18).

If the cassette 36 is not loaded, or the cassette 36 is loaded in an improper orientation, like loaded in not predetermined orientation (NO at S16), a message indicating that the cassette 36 is loaded in an improper orientation is also displayed on the monitor 64 (S19). In this case, the image capturing using the imaging apparatus 12 is not allowed (S20).

As explained above, the markers 48, 49, 55, 56 are attached to the conventional X-ray imaging system, and the cassette 36 is provided with the reflective optical sensors 41 for detecting the marker. Therefore, the present invention is applicable to the conventional X-ray imaging apparatus 12 with ease.

Since the markers 48, 49, 55, 56 are arranged near the openings through which the cassette 36 is loaded, the markers 48, 49, 55, 56 can be easily attached without reaching to a depth of the tale 18 or the holder 21.

In the explanation of the operation process of the X-ray imaging system 11, the loading state such as the loading orientation of the cassette 36 is detected at predetermined time intervals once the power is turned on. In addition to this, the loading state of the cassette 36 is detected right before the image capturing. Here, "right before the image capturing" means the time after the pre image capturing is performed, or the time after the emission of the visible light by the collimator for confirming the area being irradiated with the X-ray is performed.

[Second Embodiment]

Sensors in this embodiment are magnetic sensors (not shown) each of which judges presence of magnetism. The marker of this embodiment carries information of 3 bits, in which 1 bit is represented by presence of magnet, as shown in FIG. 8. Note that explanation of configuration and operation same as those of the first embodiment is omitted, and those different from other embodiments will be explained below.

[Third Embodiment]

Sensors in this embodiment are magnetic sensors (not shown) each of which judges magnetic pole. The marker of this embodiment carries information of 3 bits, in which 1 bit is represented by N pole or S pole, as shown in FIG. 9.

[Fourth Embodiment]

Figure 10:
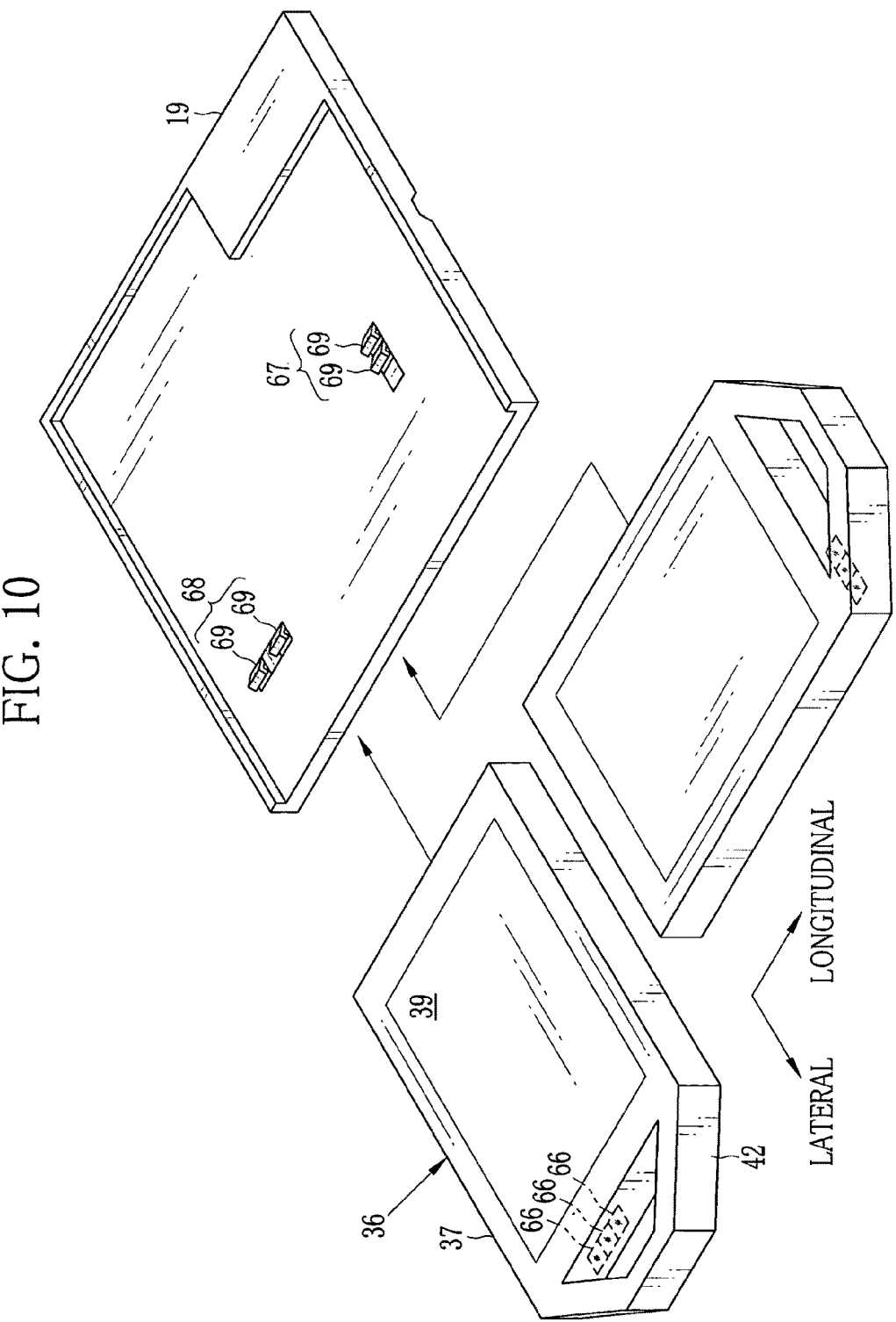
FIG. 10 is an explanatory view of push button switches each of which detects presence of pressure, and markers of 3 bits, in which 1 bit is represented by a presence of a plate spring pressing the push button switch.

As shown in FIG. 10, three push button switches 66, each of which judges presence of pressure, are arranged on the cassette body 37. Markers 68, 68 are attached to the tray 19. The marker 67, 68 are formed with a pressing member (e.g., plate spring) 69 which presses the push button switch 66. The markers 67, 68 carry information of 3 bits, in which 1 bit is represented by presence of the pressing member 69. Markers (not shown) formed with the pressing member 69, like the markers 67, 68, are attached to the holder 21.

[Fifth Embodiment]

In this embodiment, each marker carries information of 2 bits, in which 1 bit is represented by black or white. Two reflective optical sensors 41 are arranged on the cassette body 37 (not shown). As shown in FIG. 11, the marker represents the state that the cassette 36 is loaded in the table 18 for the supine-posture imaging in the longitudinal orientation with 2 bits of black and black in this arrangement. The marker represents the state that the cassette 36 is loaded in the table 18 for the supine-posture imaging in the lateral orientation with 2 bits of black and white in this arrangement. The marker represents the state that the cassette 36 is loaded in the holder 21 for the upright-posture imaging in the longitudinal orientation with 2 bits of white and black in this arrangement. The marker represents the state that the cassette 36 is loaded in the holder 21 for the upright-posture imaging in the lateral orientation with 2 bits of white and white in this arrangement.

[Sixth Embodiment]

Figure 12A:
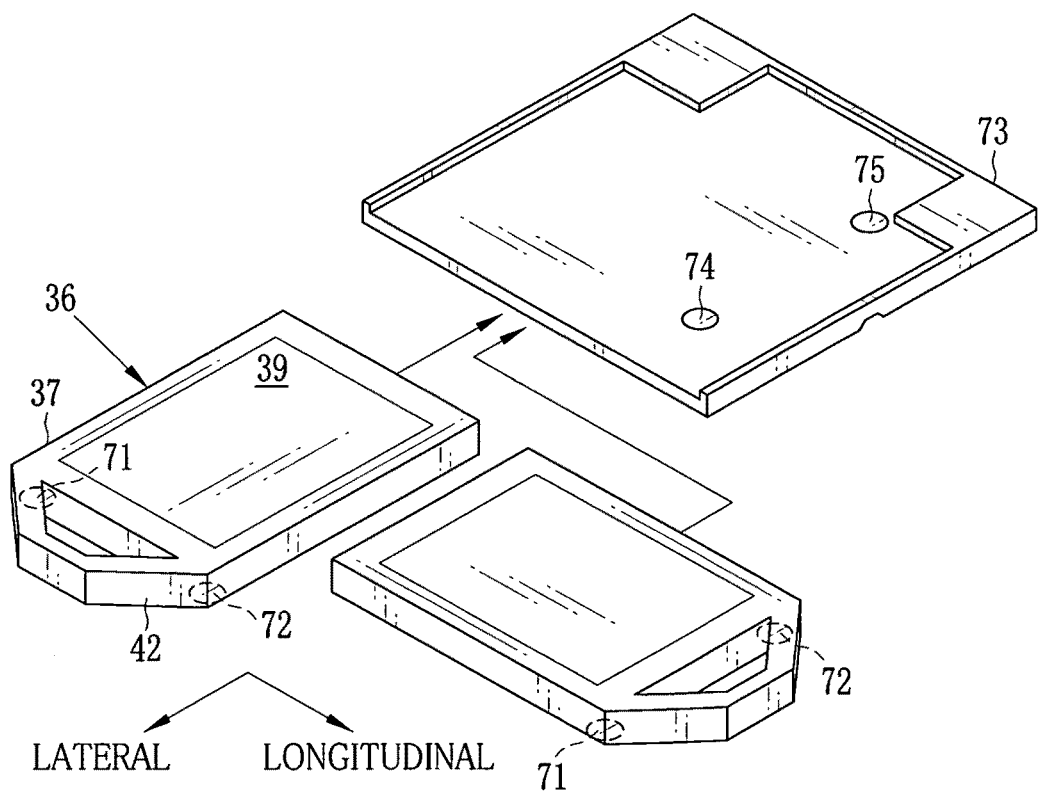
FIGS. 12A and 12B are explanatory views of a cassette loading orientation detection device having a configuration in which magnetic sensors detect magnetism of markers.
Figure 12B:
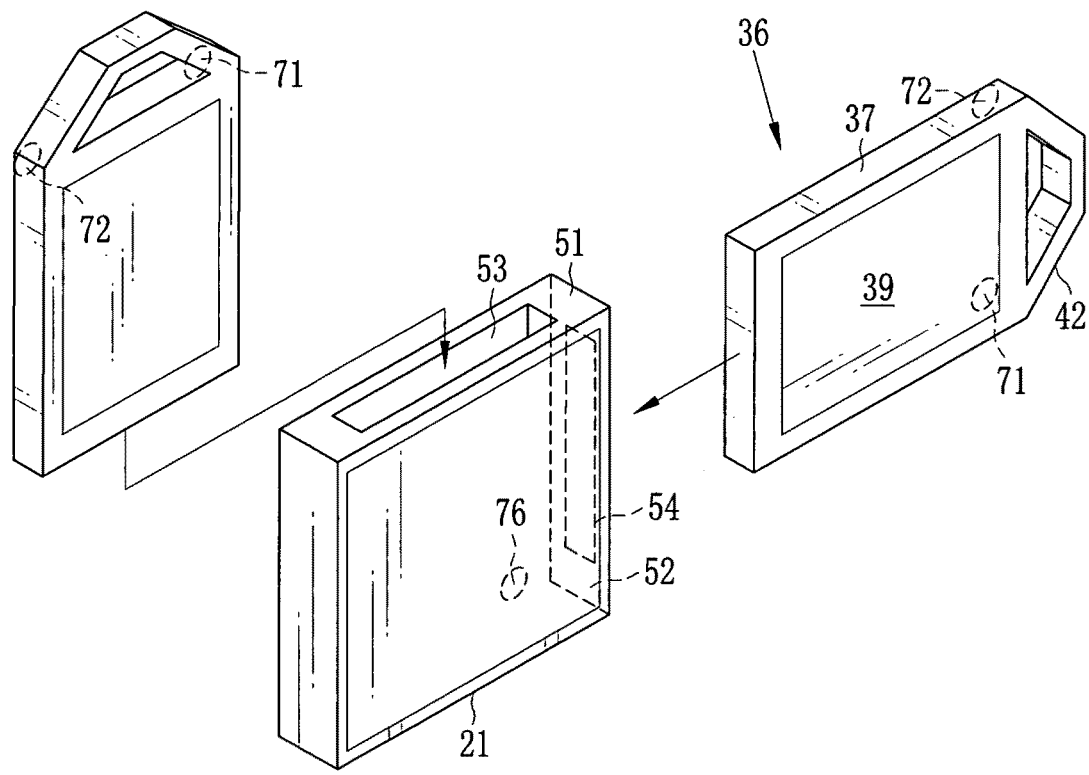

In this embodiment, two magnetic sensors for judging presence of magnetism are disposed in two different positions. As shown in FIGS. 12A and 12B, magnetic sensors 71, 72 are disposed at the upper end on each side of the rear surface, which is opposite to the detection surface 39, of the cassette body 37.

As shown in FIG. 12A, a magnet 74 is attached on an upper surface of a tray 73 for the supine-posture imaging in such a position to face the magnetic sensor 71 of the cassette 36 loaded in the longitudinal orientation as well as the magnetic sensor 72 of the cassette 36 loaded in the lateral orientation. In addition, a magnet 75 is attached to the upper surface of the tray 73 in such a position to face the magnetic sensor 72 of the cassette 36 loaded in the longitudinal orientation.

The magnetism of the magnet 74 is detected by the magnetic sensor 71 of the cassette 36 loaded in the longitudinal orientation as well as the magnetic sensor 72 of the cassette 36 loaded in the lateral orientation. The magnetism of the magnet 75 is detected by the magnetic sensor 72 of the cassette 36 loaded in the longitudinal orientation.

As shown in FIG. 12B, a magnet 76 is attached inside of the holder 21 for the upright-posture imaging in such a position to face the magnetic sensor 71 of the cassette 36 loaded in the lateral orientation. The magnetism of the magnet 76 is detected by the magnetic sensor 71 of the cassette 36 loaded in the lateral orientation.

The detection results using the magnetic sensors 71, 72 are output to the controller 61 of the console 65. As shown in FIG. 13, if the magnetism is detected by both of the magnetic sensors 71 and 72, the cassette 36 is judged as being loaded in the table 18 for the supine-posture imaging in the longitudinal orientation. If the magnetism is detected by the magnetic sensor 72, but not by the magnetic sensor 71, the cassette 36 is judged as being loaded in the table 18 for the supine-posture imaging in the lateral orientation.

If the magnetism is not detected by both of the magnetic sensors 71 and 72, the cassette 36 is judged as being loaded in the holder 21 for the upright-posture imaging in the longitudinal orientation. If the magnetism is detected by the magnetic sensor 71, but not by the magnetic sensor 72, the cassette 36 is judged as being loaded in the holder 21 for the upright-posture imaging in the lateral orientation.

[Seventh Embodiment]

Figure 14A:
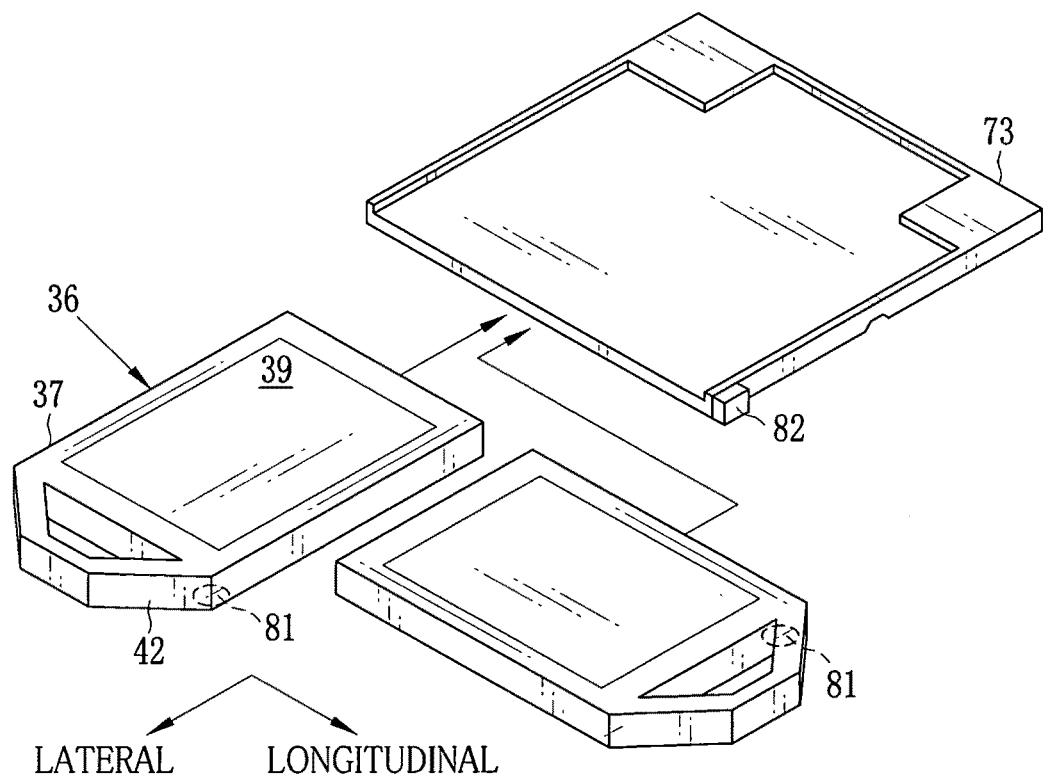
FIGS. 14A and 14B are explanatory views of a cassette loading orientation detection device having a configuration in which a sensor receives radio waves from markers.
Figure 14B:
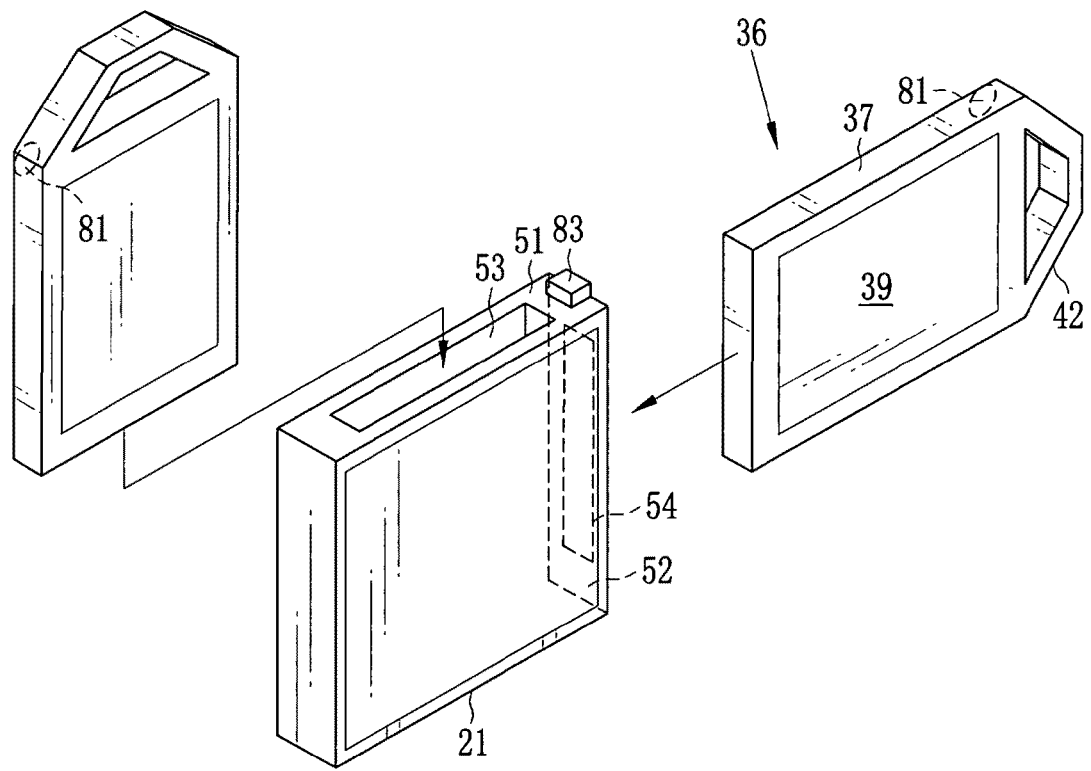

As shown in FIGS. 14A and 14B, a radio wave sensor 81 for receiving radio waves is disposed at the upper end on right side of the rear surface, which is opposite to the detection surface 39, of the cassette body 37.

As shown in FIG. 14A, a marker 82 which sends radio waves is attached on the right side of the tray 73 for the supine-posture imaging. The marker 82 is located near the opening of the tray 73 through which the cassette 36 is loaded. Transmission area of the radio waves from the marker 82 is limited within approximately 10 mm, and thus it is not received with the sensor 81 of the cassette 36 loaded in the longitudinal orientation, but is received with the sensor 81 of the cassette 36 loaded in the lateral orientation. The radio waves sent from the marker 82 includes information indicating that the cassette 36 is loaded in the table 18 for the supine-posture imaging, and the loading orientation is the lateral orientation.

As shown in FIG. 14B, a marker 83 which sends radio waves is attached on the top surface of the holder 21 for the upright-posture imaging. Transmission area of the radio waves from the marker 83 is limited within approximately 10 mm, and thus it is not received with the sensor 81 of the cassette 36 loaded in the longitudinal orientation, but is received with the sensor 81 loaded in the lateral orientation. The radio waves sent from the marker 83 includes information indicating that the cassette 36 is loaded in the holder 21 for the upright-posture imaging, and the loading orientation is the lateral orientation.

The detection result using the sensor 81 is output to the controller 61 of the console 65. If the radio waves from the markers 82 and 83 are received, the cassette 36 is judged as being loaded in the lateral orientation. If the radio waves from the markers 82 and 83 are not received, the cassette 36 is judged as being loaded in the longitudinal orientation.

If the radio waves from the marker 82 are received, the cassette 36 is judged as being loaded in the table 18 for the supine-posture imaging, and if the radio waves form the marker 83 are received, the cassette 36 is judged as being loaded in the holder 21 for the upright-posture imaging.

[Eighth Embodiment]

Figure 15:
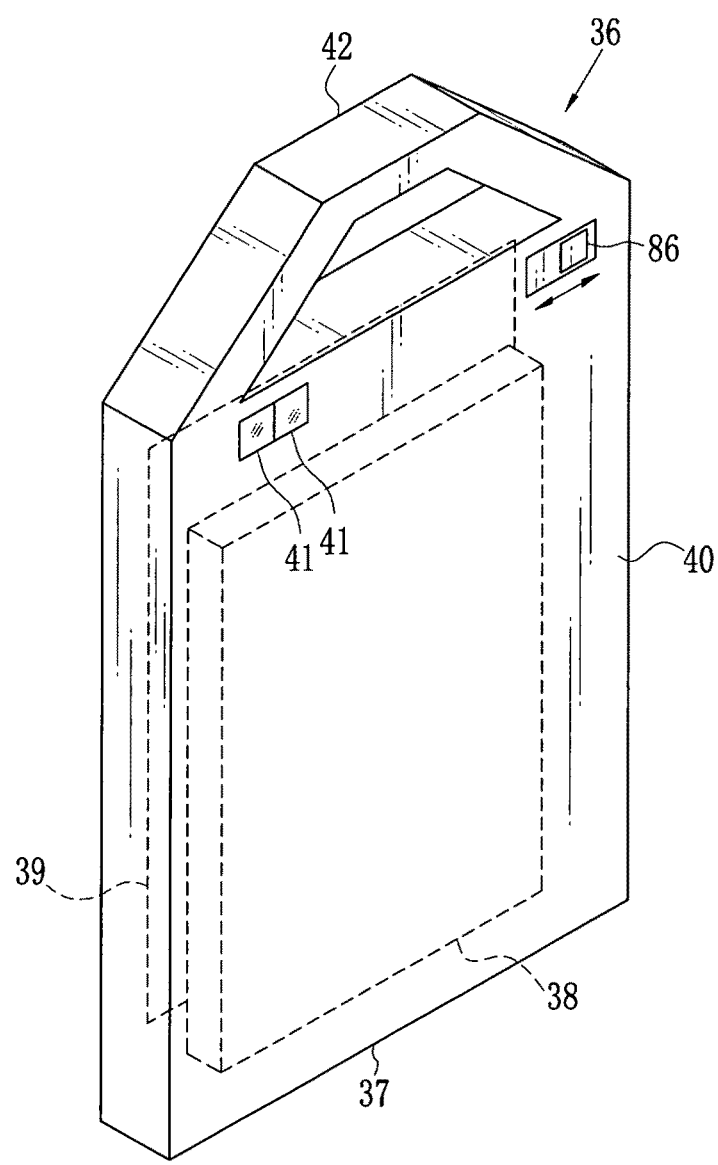
FIG. 15 is an external perspective view of a cassette for X-ray imaging having a setup switch for setting the imaging platform to which the cassette is loaded.

As shown in FIG. 15, two reflective optical sensors 41 are arranged at the upper end on left side of the rear surface 40 of the cassette body 37. A marker (not shown) having information of 2 bits is attached to the tray 19 for the supine-posture imaging and the holder 21 for the upright-posture imaging. The marker indicates that the cassette 36 is loaded in the longitudinal orientation or the lateral orientation.

A setup switch 86 is provided at the upper end on right side of the rear surface 40 of the cassette body 37. The setup switch 86 is for setting the table 18 for the supine-posture imaging or the holder 21 for the upright-posture imaging as the imaging platform of the cassette 36 being loaded.

The setup switch 86 slides right and left. When the setup switch 86 is set to the left, the table 18 is set as the imaging platform to which the cassette 36 is loaded, and when the setup switch 86 is set to the right, the holder 21 is set as the imaging platform to which the cassette 36 is loaded. Information of the setup using the setup switch 86 is output to the controller 61 of the console 65 together with the detection signal of the reflective optical sensors 41.

Although the information is represented by 3 bits in the second to fourth embodiments, the information may be represented by 2 bits. Moreover, the cassette 36 in the second to fourth embodiments may be provided with the setup switch 86.

In any of the above embodiments, the image capturing can be allowed by the controller 61 in spite of the loading orientation of the cassette 36. In this case, the controller 61 rotates the X-ray image as needed to display it on the monitor 64 according to the loading orientation of the cassette 36. Instead of rotating the X-ray image by the controller 61, it is also possible to provide the cassette 36 with a controller. In this case, an image signal is output to the console 65 such that the X-ray image is displayed on the monitor 64 in a desired direction. Here, the controller provided to the cassette 36 works as a judgment section for judging the direction of the X-ray image.

In any of the above embodiments, the positions of the sensor and the marker may be switched with each other, that is, the marker is provided to the cassette 36 and the sensor is attached to the table 18 and the holder 21.

In the above embodiments, the X-ray is used as an example of the radiation. However, the present invention is not limited to this, and may be applicable to the case using α-rays, γ-rays, and the like.

Various changes and modifications are possible in the present invention and may be understood to be within the present invention.

What is claimed is:

1. A cassette for radiographic imaging, comprising:
   a cassette body storing a radiation detector, said cassette body being capable to be loaded in a conventional imaging platform in more than one loading orientation; and
   a sensor provided to said cassette body for detecting loading information including at least said loading orientation from a marker attached to said conventional imaging platform, or a marker provided to said cassette body for making a sensor, attached to said conventional imaging platform, detect loading information including at least said loading orientation.

2. The cassette for radiographic imaging of claim 1, wherein when said marker is attached to said imaging platform, said marker is located in such a position that said loading information is detected by said sensor of said cassette body loaded in each loading orientation, or when said sensor is attached to said imaging platform, said sensor is located in such a position to detect said loading information from said marker of said cassette body loaded in each loading orientation.

3. The cassette for radiographic imaging of claim 1, wherein said loading information includes information representing whether said imaging platform is an upright-posture imaging platform or a supine-posture imaging platform.

4. The cassette for radiographic imaging of claim 1, further comprising:
   a judgment section for judging a direction of a radiographic image of radiation detected by said radiation detector, based on said loading orientation detected by said sensor.

5. The cassette for radiographic imaging of claim 1, wherein said sensor or said marker provided to said cassette body is located at an upper end side of said cassette body.

6. The cassette for radiographic imaging of claim 1, wherein said loading information is represented by multiple-bit patterns.

7. The cassette for radiographic imaging of claim 6, wherein said sensor is one of the following sensors or switch:
   a reflective optical sensor for judging presence of reflection light, wherein said marker representing 1 bit with black or white;
   a magnetic sensor for judging presence of magnetism, wherein said marker representing 1 bit with presence of magnet;
   a magnetic sensor for judging magnetic pole, wherein said marker representing 1 bit with N pole or S pole; and
   a push button switch for judging presence of pressure, wherein said marker representing 1 bit with presence of a pressing member which presses said sensor.

8. The cassette for radiographic imaging of claim 1, wherein said marker sends said loading information via radio waves and said sensor receives said radio waves from said marker.

9. The radiographic imaging cassette of claim 1, further comprising:
   a setup switch for setting either one of an upright-posture imaging platform and a supine-posture imaging platform as said imaging platform.

10. A cassette loading orientation detection device, comprising:
    a cassette body storing a radiation detector, said cassette body being capable to be loaded in a conventional imaging platform in more than one loading orientation;
    a marker attached to said conventional imaging platform, for making said loading orientation being detected; and
    a sensor provided to said cassette body, for detecting said loading orientation from said marker.

11. The cassette loading orientation detection device of claim 10, further comprising:
    a judgment section for judging a direction of a radiographic image of radiation detected by said radiation detector, based on said loading orientation detected by said sensor.

12. A cassette loading orientation detection device comprising:
    a cassette body storing a radiation detector, said cassette body being capable to be loaded in a conventional imaging platform in more than one loading orientation;
    a marker provided to said cassette body, for making said loading orientation being detected; and
    a sensor attached to said conventional imaging platform, for detecting said loading orientation from said marker.

13. The cassette loading orientation detection device of claim 12, further comprising:
    a judgment section for judging a direction of a radiographic image of radiation detected by said radiation detector, based on said loading orientation detected by said sensor.

* * * * *